United States Patent [19]
Lemire

[11] Patent Number: 5,876,339
[45] Date of Patent: Mar. 2, 1999

[54] APPARATUS FOR OPTICAL BREAST IMAGING

[76] Inventor: Robert Lemire, 21 Carriage Dr., Kings Park, N.Y. 11754

[21] Appl. No.: 780,879

[22] Filed: Jan. 9, 1997

[51] Int. Cl.$^6$ ....................................................... A61B 5/00
[52] U.S. Cl. .......................... 600/425; 600/427; 600/473; 600/476
[58] Field of Search .................................... 600/473–478, 600/411, 427, 425

[56] References Cited

U.S. PATENT DOCUMENTS

| | | | |
|---|---|---|---|
| 5,034,010 | 7/1991 | Kittrell et al. | 600/478 |
| 5,555,885 | 9/1996 | Chance | 600/477 |

OTHER PUBLICATIONS

*Photonics Spectra*, "Powerful Solid–State Lasers Steal Ion's Thunder," Apr. 1996.
C. Bouchez, *Daily News*, "For Cancer, A Better Picture," Oct. 27, 1996.
Dr. D. F. Preston, *Diagnostic Imaging, The Newsmagazine of Radiology, MRI, Nuclear Medicine and Ultrasound*, "Alternatives to Mammography Show Promise", Sep. 1996.
*Business Wire*, "Imaging Diagnostics Systems, Inc. announces use of a revolutionary laser", Jan. 29, 1996.
*Medical Imaging News*, "IDSI to Test CT Laser Mammography Within Two Weeks", vol. 5, No. 06, Feb. 9, 1996.
*Investor's Business Daily*, "Investor's NewsWire", Apr. 4, 1996.
*PR Newsire*, "Women Find Breast Exams by New CT Laser Device a Welcome Change From Traditional Mammography (Only Company of 1400 Exhibitors at RSNA Pioneering Laser Imaging Technology)," Dec. 3, 1996, pp. 2–3.
S.A. Advisory Research, Nov. 1996.
Imaging Diagnostic Systems Brochure entitled, "Imaging Diagnostic Systems presents an update on CT Laser Mammography", 1996.

Richard J. Grable, "Medical Optical Imaging (MOI): A Status Review," Apr. 21, 1995, Revised Feb. 19, 1996, pp. 1–8.

Richard J. Grable, *Laser Focus World*, "Optical Tomography Improves Mammography" Oct. 1996.

(List continued on next page.)

*Primary Examiner*—Ruth S. Smith
*Attorney, Agent, or Firm*—Proskauer Rose LLP

[57] ABSTRACT

A breast imager generates an image of a breast and determines if a suspicious growth is present in the breast. The optical breast imager includes a "breast box" in which a patient's breast may be enclosed, a transmitter/detector device, and a data acquisition system. The "breast box" includes four optical arrays. The "breast box" defines an adjustable volume which may accommodate different sized breasts. The arrays may be used to send optical energy into the "breast box" or to receive optical energy which has been transmitted into the "breast box". The transmitter/detector device has four optical arrays corresponding to "breast box" imaging arrays. The transmitter/detector device may also have one or more optical energy transmitters and optical energy detectors. The transmitter (or transmitters) may transmit optical energy into a location on a transmitter/detector array. The optical energy is sent into the "breast box" via the corresponding "breast box" imaging array. Energy which passes through and/or is scattered by the tissue strikes the surface the "breast box" imaging arrays and is sent to the transmitter/detector device arrays, where the energy may be detected by an optical detector. The operation of the transmitters and detectors may be synchronized so that optical energy may be transmitted from a known location at a known time and the locations from which that transmitted energy is subsequently detected may be determined. The detected energy data is sent to the data acquisition system for processing.

35 Claims, 9 Drawing Sheets

OTHER PUBLICATIONS

*PR Newswire*, "Financial News", Dec. 2, 1996.
*The Orange County Register*, "Laser Testers May Shed Light on Cancers", Nov. 6, 1996, p.E01.
*Sun–Sentinel*, "Health Care", Aug. 20, 1996, p. 1D.
*PR Newswire*, "Financial News", Nov. 22, 1996.
*Christensen's Physics of Diagnostic Radiology* (4th Ed.) pp. 301–302.
*Business Journal–Jacksonville*, "Business Dateline"; vol. 11; No. 43; p. 5.
*New Technology Week*, "BMDO Dual Effort to Duel Breast Cancer", No. 29, vol. 10; Jul. 15, 1996, ISSN: 0894–0789.
*Healthcare Technology & Business Opportunities*, "Multiple Business Opportunities"; vol. 18; No. 6, Jun. 15, 1996.

*Sacramento Bee*, "Knowledge Is Power", Oct. 24, 1996, p. D1.

*Life Sciences & Biotechnology Update*, "Early Detection of Breast Cancer and its Recurrence Using Near–Infrared Time–Resolved Spectrophotometry", Jul. 1, 1996; vol. 96; No. 7.

CNN, *CNN Prime News* (transcript), "Low Intensity Laser Shows Lifesaving Promise", Oct. 20, 1996.

*Federal Technology Report*, Aug. 29, 1996, p. 3.

M. Schnall, MD, PhD, "MRI's Role in Breast Imaging," Apr. 1996, pp. 25–26.

APPARATUS FOR OPTICAL BREAST IMAGING

BACKGROUND OF THE INVENTION

1. Field of the Invention

The present invention relates to medical imaging and, more particularly, to a method and apparatus for breast imaging using non-ionizing photons in the electromagnetic spectrum, such as optical energy.

2. Discussion of Related Art

According to the American Cancer Society, in 1996 184,300 women will be diagnosed with breast cancer and 44,300 women will die from breast cancer. The ACS estimates that 1,500,000 women will be diagnosed and more than 500,000 women will die of breast cancer in the 1990's. Early breast cancer detection increases the patient's chances of surviving the cancer. Thus, early detection is a major factor in saving the lives of breast cancer patients. The five-year survival rate is 96% for women having early detection of breast cancer. Although experts agree that a mammogram is the single best means of early breast cancer detection, in 60% of all women diagnosed with breast cancer, early detection was missed due to low-contrast mammography images.

1. Current Breast Imaging Methods

Mammography is the radiological examination of the human breast. It is generally accepted that mammography is an effective and reliable procedure in the early detection of breast cancer. Mammography is typically performed using x-ray or other traditional film/screen techniques. However, these techniques do not always provide adequately high-quality images to detect cancer, particularly in the relatively large population of women having radiodense breast tissue (younger women, for example, tend to have radiodense breast tissue). Mammograms require high-quality images because the tissue density between adipose (fatty), glandular, calcified, or cancerous tissue is less diverse than, for example, flesh and bone. Thus, "subtler" contrasts are required to distinguish between these types of tissue.

Traditional film mammograms do not provide these subtler contrasts. Film mammograms have a non-linear response to x-ray exposure. That is, for example, doubling the x-ray exposure of film or halving the breast density, does not result in an image that is twice as bright. As a result, a single traditional film x-ray exposure often does not show the entire tonal range of a patient's breast tissue. Often, a radiologist may take exposures at different energy levels to provide images with different contrasts. This exposes the patient to several doses of x-rays, which are a known cause of cancer.

Other drawbacks are caused by the poor contrast of film mammograms. One of these drawbacks is that it is difficult to detect masses in patient's having breast implants. A second drawback is that it is difficult to discern between benign and malignant microcalcifications and tumors. This latter drawback results in thousands of unnecessary invasive procedures to remove growths which are later determined to be benign. If a mammogram could allow a radiologist to distinguish more clearly between benign and malignant tissue, many of those procedures would be prevented.

FIG. 1 illustrates a conventional mammography machine using a traditional film technique. The conventional mammography machine 50 has an x-ray tube 52 which emits x-rays and an image receptor 54 which receives the x-ray radiation. During use, a breast 56 is compressed between a compression plate 58 which holds the breast in position, and a bucky tray 60, which sits on top of the image receptor, supports the breast 56 and houses a grid 62. The breast is typically compressed very tightly by the compression plate. The compression is applied to make the breast have as uniform a shape as possible to obtain an accurate image. In addition to being very uncomfortable for the patient, some experts believe that this compression may release existing cancer cells into the vascular system of women who may already have undetected breast cancer.

Beneath the grid is a scintillator 64 which generates visible light when excited by x-rays. A film 66 is placed below the bucky tray and scintillator and on top of a radiation detector 68 used for automatic exposure control, such as an ionization chamber or a solid state sensor. X-ray radiation passes through the breast tissue and strikes the scintillator 64. The scintillator generates visible light according to the x-ray striking it. The visible light enters the image receptor and exposes the film. After the film is exposed, it must be developed before it may be viewed. Areas on the developed film not exposed to the x-ray radiation result in a light area on the film indicating that the radiation did not pass through the tissue. This is an indication of a mass or other x-ray blocking body.

Digital mammography which employs a solid state electronic imager in place of film is an emerging technology in the detection of breast cancer. Digital mammography offers several advantages, such as shorter procedure times, improved image quality, decreased health care costs because digital mammograms provide early detection; and lower radiation exposure. Digital mammography also faces severe technical challenges. Soft-tissue breast imaging has the most stringent imaging requirements of all radiological imaging. Two reasons for this are the slight difference in densities between the tissue types found in breasts (adipose, glandular, calcified, and cancerous) and the relatively small size of breast tumors in their initial stages. As a result, mammography requires very fine pixel dimensions (e.g., less than 40 microns) and a high contrast dynamic range (14 bits, i.e., $2^{14}$ or 16,384 tone levels) over a large area (i.e., 24 cm×30 cm). The American College of Radiology recommends an image resolution of 11 to 13 line pairs per millimeter. This means that the image should be sharp enough to distinguish between 11 to 13 pairs of white and black lines in a one millimeter space.

In any event, digital mammography still requires uncomfortable breast compression and exposure to potentially harmful, cancer-causing x-ray radiation.

Magnetic Resonance Imaging (MRI) has also been used for breast imaging. Although MRI has been found to provide acceptable resolution images, an MRI machine is very expensive. The MRI machine is a limited resource which may best be used for other purposes. Breast imaging using MRI may be too expensive to be practical. This cost issue is vitally important. Experts currently disagree about the age at which a woman should begin having annual mammograms. Although some consideration of this debate involves the amount of radiation a woman is exposed to, a great concern is that of health care insurers (such as HMOs): health care insurers look for a prevention costs v. medical benefit costs "break even" point. If statistics show that it will cost more to pay for mammographies for all women of a certain age than the medical costs for medical treatment of women of that age expected to develop breast cancer, regular mammograms are not recommended. Although this may make economic sense, it does not make sense to the younger women at the lower end of the statistical analysis who have undetected breast cancer. Therefore, a more expensive alternative to conventional mammography may not result in increased detection, prevention, and saved lives.

2. Breast Imaging Using Non-Ionizing Light

Opto-electronics have been used for breast imaging. For example, near-red spectroscopy uses non-ionizing radiation which passes easily through breast tissue and may be tolerated in relatively large doses. Early efforts to provide optical breast imaging were unsuccessful because light scattering was not measurable and the resultant image quality was poor.

Some infrared (IR) imaging devices use IR cameras to detect "hot spots" in the breast, are hand-held devices, or require the injection of dyes into the patient. Imaging Diagnostics Systems Inc. of Plantation, Florida, has developed a laser tomography imaging device which uses a single laser which revolves around a patient's breast. Power, control, and output signals are exchanged from the rotating laser device to the rest of the machine using slip rings, which may be noisy; DC power supplies are mounted on the rotating device. The device includes no adjustability for different sized breasts.

Lasers have recently been considered as useful diagnostic tools because light travels differently depending upon what it travels through. Obstacles in the way of laser photons may cause the photons to scatter or be absorbed. For example, cancerous cells contain more hemoglobin than non-cancerous cells and absorb light more readily. Cells having a high density (another sign of cancer) tend to scatter photons. These scatter and absorption characteristics may vary depending on the wavelength of light used.

It is an object of the present invention to provide a method and device for breast imaging that does not use ionizing radiation, such as x-rays.

It is another object of the present invention to provide a breast imaging device that does not require the breast to be compressed.

It is yet another object of the present invention to provide a device which permits inexpensive breast imaging.

It is a further object of the present invention to provide a breast imaging device that can detect very small growths.

It is even a further object of the present invention to provide a breast imaging device that can distinguish between types of cell growths and thus reduce the need for unnecessary biopsy procedures.

It is yet a further object of the present invention to provide a breast imaging device that allows real-time imaging during surgical procedures, such as needle biopsies.

SUMMARY OF THE INVENTION

These and other objects of the present invention are provided by a medical imaging device, such as an optical breast imaging device which generates an image of a breast and, using photon absorption and scattering data from one or more energy wavelengths, may determine if a suspicious growth is present in an area of the breast. A preferred embodiment of an optical breast imaging device according to the present invention includes a "breast box" in which a patient's breast may be enclosed, a transmitter/detector device, and a data acquisition system.

A preferred embodiment of the "breast box" includes a number of optical imaging arrays, each preferably comprising a number of optical fibers (or fiber optic bundles). Illustratively, four arrays are provided wherein the side and top imaging arrays are moveable to define a box-like volume which may accommodate different sized breasts. The optical fibers may be used to send optical energy into the "breast box" or to receive optical energy which has been transmitted into the "breast box".

In a preferred embodiment, the transmitter/detector device comprises a number of optical arrays comprising a number of optical fibers (or fiber optic bundles). Preferably, each array in the transmitter/detector device corresponds to an imaging array in the "breast box". Each optical fiber in each imaging array of the "breast box" may be optically connected through fiber optic connections to an optical fiber in one of the transmitter/detector arrays. The diameter of each fiber in the transmitter/detector may be larger than the diameter of the corresponding fiber in the "breast box" imaging array. That is, each optical fiber may be tapered so that the diameter of the optical fiber is larger in the transmitter/detector device and smaller in the "breast box" imaging array.

The transmitter/detector device may also preferably include one or more optical energy transmitters and optical energy detectors. The transmitters may be, for example, any suitable optical energy transmission source, such as a laser light source or light emitting diode. The optical detectors may be any suitable detector for detecting the transmitted energy. The detectors may be, for example, photodiodes or charged coupled devices. The transmitter (or transmitters) may transmit optical energy into a particular fiber in a transmitter/detector array. This energy may then be transmitted into the "breast box" via the corresponding fiber in the "breast box" imaging array. The transmitted energy may then pass through, be absorbed, or be scattered by the patient's breast tissue. The energy which passes through and/or is scattered strikes the surface of one or more of the "breast box" imaging arrays and is optically sent via the fiber optic connections to the transmitter/detector device arrays, where the energy may be detected by an optical detector.

The transmitter/detector device may also include a positioner which permits transmitters and detectors to be selectively located at preselected locations along the surfaces transmitter/detector device arrays. The motion of the positioner and the operation of the transmitters and detectors may be synchronized so that optical energy may be transmitted from a known location at a known time and the locations from which that transmitted energy is subsequently detected may be determined.

Preferably, the transmitter/detector device arrays may be arranged in any desired manner. The arrays may be laid out in a two dimensional arrangement and the positioner may move in only two directions (such as in the horizontal and vertical directions). This permits three dimensional breast scanning to be performed using only two dimensional movement of the transmitters and detectors. Also, the transmitter/detector device arrays provide a "scaled up", optical conduit to the "breast box". That is, one or more optical fibers in the transmitter/detector device arrays receive transmitted optical energy, send the energy to the "breast box" imaging array via an optical coupling, and the corresponding "breast box" imaging arrays fiber (or fibers) send the energy into the "breast box" and thus the patient's breast tissue. The energy exiting the patient's breast tissue is received by the fibers in the "breast box" imaging arrays and the energy is sent to the transmitter/detector device arrays. The energy exits the corresponding fibers in the transmitter/detector device arrays and is detected by an optical energy detector.

In a preferred embodiment, the transmitter/detector device is connected to a data acquisition system. The data acquisition system may be, for example, a computer. The data acquisition system coordinates the transmission and detection of the optical energy and converts the detected energy into useful information, such as an image. In a preferred embodiment, a 3-dimensional grid-like image of the patient's breast may be generated. The data acquisition system may be connected to an output device, such as a monitor, VCR, or other memory storage device.

The invention preferably operates in the following manner. A patient's breast is placed on the bottom array. The side and top arrays are then positioned to gently touch the sides of the patient's breast. A block, such as a foam block, may be used to conform the end of the breast to the area defined inside the arrays. Little or no compression is necessary. The arrays (and optional block) create a "breast box" which encloses a breast that is ready for imaging. Next, optical energy is transmitted in a synchronized manner so that the optical energy is scanned throughout the patient's breast. In a preferred embodiment, two substantially orthogonal transmitters are simultaneously fired to "trace" a 3-dimensional grid throughout the patient's breast comprising of a number of "blocks". Preferably, the transmission is performed at the transmission/detection device. One or more optical transmitters may be positioned along the transmission/detector array. The optical energy is received by a fiber on the transmitter/detector array and is sent to a corresponding fiber in a "breast box" array, where the optical energy is transmitted into the patient's breast tissue.

The optical energy exiting the patient's breast along this grid is detected by the optical energy detector arrays. Data regarding the optical energy input into and exiting out of the breast is provided to the data acquisition system. Using well-known computer-tomography algorithms, the amount of energy entering and leaving each "block" of the 3-D grid may be determined. This information indicates the amount of energy that was absorbed, scattered, or passed through the "block" and may be used to generate an image of that "block" and/or may be used for diagnosis. For example, an image of the breast tissue may be generated or photon absorption or scattering information may be used to determine the presence of a suspicious mass. Also, the breast may be imaged using more than one wavelength. The difference in scatter and absorption properties for the different wavelengths may be used to determine the make-up of a suspicious mass.

The entire process is safe and comfortable for the patient. The patient is not exposed to ionizing radiation nor is the patient's breast subject to uncomfortable (and possibly dangerous) compression. The resultant image does not have the contrast problems associated with x-ray film. Moreover, the resultant data is digital and may be processed, stored, and transmitted in the same manner as other digital data. Also, because the patient is not exposed to harmful radiation, the device may be safely used for extended periods of time during surgical procedures, such as real-time imaging and guiding of needles during breast biopsies.

BRIEF DESCRIPTION OF THE DRAWINGS

The present invention is described with reference to the following figures.

DETAILED DESCRIPTION OF PREFERRED EMBODIMENTS

The present invention is described with reference to the following sections:

I. Overview of the Invention: An overview of the invention is provided with reference to FIG. 2.
II. The "Breast Box": The "breast box" is described with reference to FIGS. 3A, 3B, 4A, and 4B.
III. The Transmitter/Detector Device: The transmitter/detector device according to a preferred embodiment of the present invention is described with reference to FIGS. 5A, 5B, 6A, 6B, 7A, 8A, and 8B.
IV. The Scanning and Detecting Processes: The scanning and detecting processes are described with reference to FIGS. 9A and 9B.
V. The Data Acquisition System: A data acquisition system is described with reference to FIG. 10.
VI. Conclusion: A conclusion is provided.

I. Overview of the Invention

Figure 1:
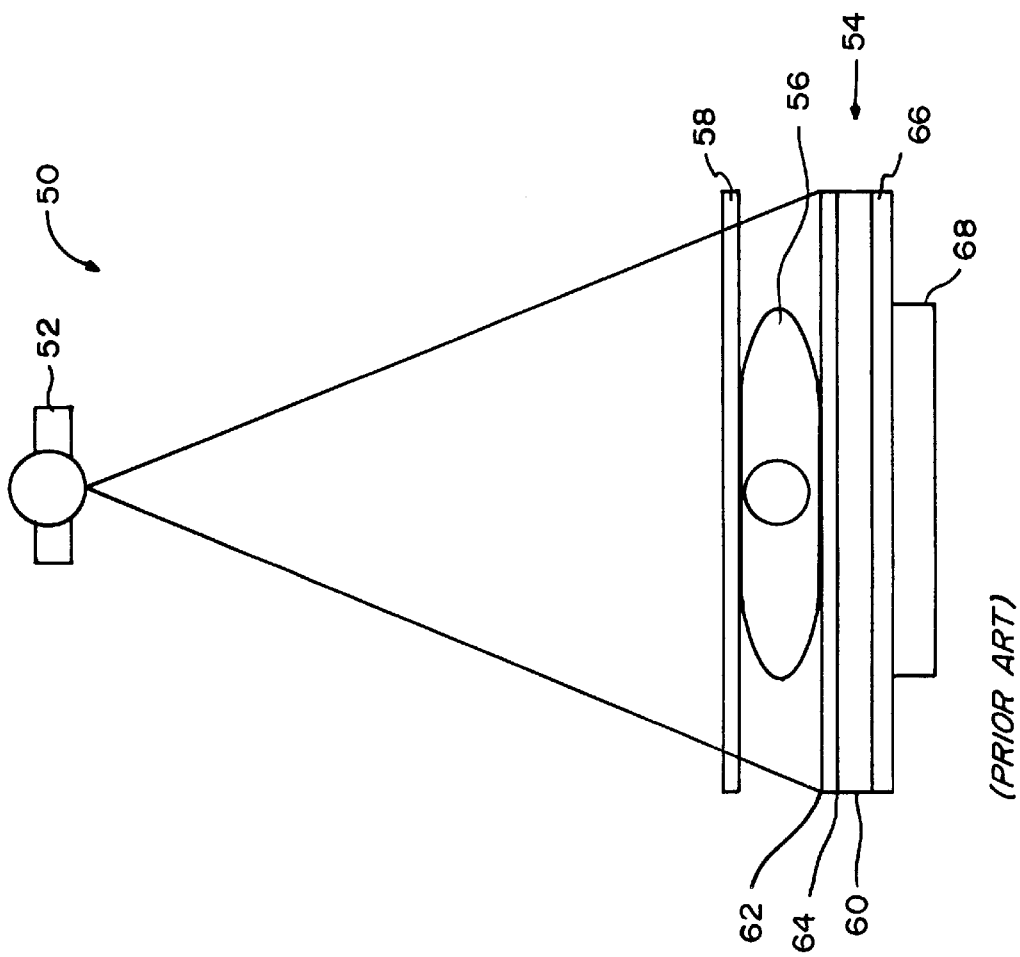
FIG. 1 illustrates a conventional mammography machine using traditional film techniques.
Figure 2:
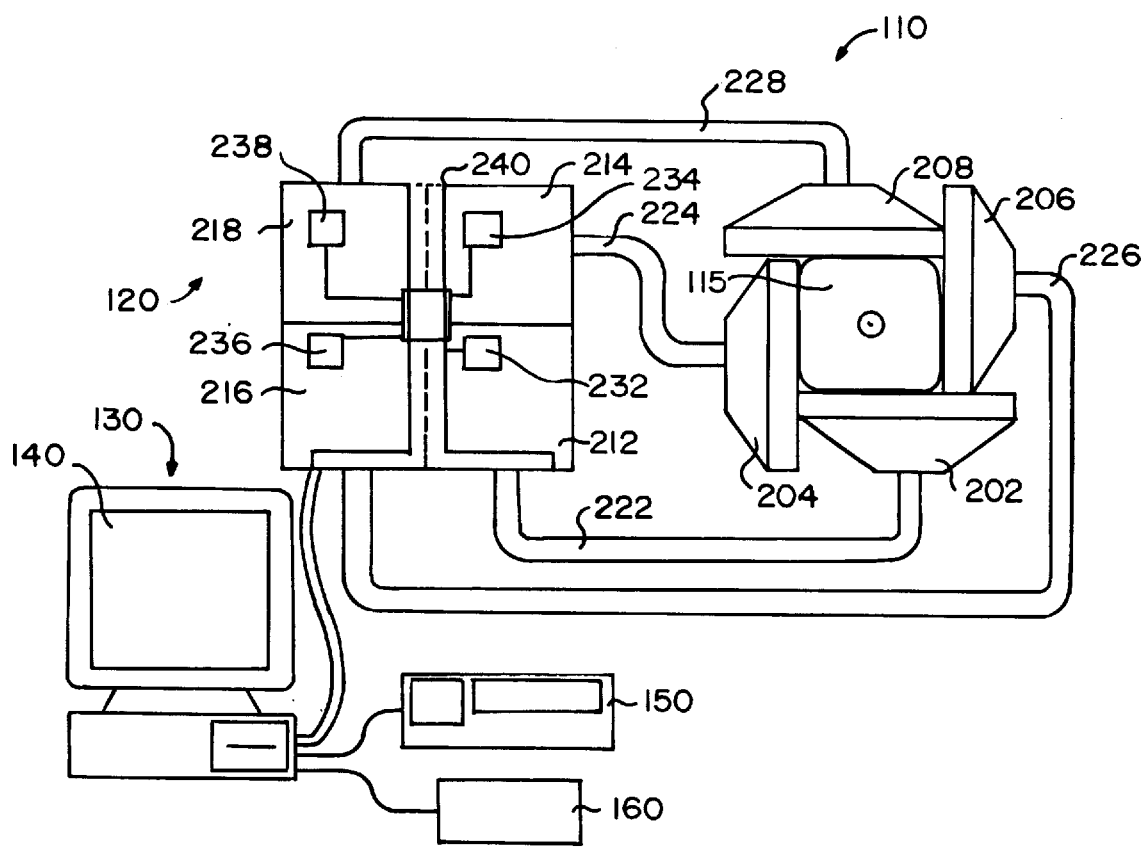
FIG. 2 illustrates a preferred embodiment of the present invention.

FIG. 2 illustrates a preferred embodiment of an optical breast imaging device 100 according to the present invention. The present invention preferably includes a "breast box" 110 in which a patient's breast 115 may be enclosed, a transmitter/detector device 120, and a data acquisition system 130.

In a preferred embodiment, the "breast box" 110 includes four optical imaging arrays 202, 204, 206, 208, each preferably having an inner surface comprising a number of (preferably closely packed) optical fibers (or fiber optic bundles). Illustratively, the side and top imaging arrays 204, 206, 208 are selectably adjustable in a manner described in detail below in order to define a box-like volume which may accommodate different sized breasts. The fibers may be used to send optical energy into the "breast box" or to receive optical energy which has been transmitted into the "breast box". The term optical energy is used herein to mean any non-ionizing electromagnetic energy, particularly energy within the infra-red, visible, and ultra-violet light spectra.

In a preferred embodiment, the transmitter/detector device 120 comprises four optical arrays 212, 214, 216, 218, each preferably comprising a number of optical fibers (or fiber optic bundles). Preferably, each array in the transmitter/detector device 120 corresponds to an imaging array in the "breast box". Each fiber in each imaging array of the "breast box" may be optically connected through fiber optic connections 222, 224, 226, 228 to the fiber in the transmitter/ detector arrays 212, 214, 216 218. The diameter of each fiber in the transmitter/detector may be larger than the diameter of the corresponding fiber in the "breast box" imaging array and need not be closely packed. That is, each optical fiber may be tapered so that the diameter of the optical fiber is larger in the transmitter/detector device 120 and smaller in the "breast box" imaging array 110. Thus, the transmitter/detector arrays may be "scaled up" versions of the "breast box" imaging arrays.

The transmitter/detector device 120 may also preferably include one or more optical energy transmitters and optical energy detectors (not shown), which may be contained on selectively positionable transmitter/detector units 232, 234, 236, 238. The transmitters may be, for example, any suitable optical energy transmission source, such as a laser light source or light emitting diode. The optical detectors may be any suitable detector for detecting the transmitted energy. The detectors may be, for example, photodiodes or charged coupled devices. The transmitter/detector units may be selectively positioned along the transmitter/detector arrays using a positioner 240. The transmitter (or transmitters) may transmit optical energy into a particular fiber in a transmitter/detector array. This energy may then be sent into the "breast box" via the corresponding fiber in the "breast box" imaging array. The transmitted energy may then pass through, be absorbed, or be scattered by the patient's breast tissue. The energy which passes through and/or is scattered strikes the surface of one or more of the "breast box" imaging arrays and is optically sent via the fiber optic connections 222, 224, 226, 228 to the transmitter/detector device arrays 212, 214, 216, 218, where the energy may be detected by the optical detectors housed on 232, 234, 236, 238.

Preferably, the transmitter/detector device arrays 212, 214, 216, 218 may be arranged in any desired manner. The arrays may be laid out in a two dimensional arrangement and the positioner 240 may move in only two directions (such as in the horizontal and vertical directions). This permits three dimensional breast scanning to be performed using only two dimensional movement of the transmitters and detectors. Also, the transmitter/detector device arrays 212, 214, 216, 218 provide a "scaled up", optical conduit to the "breast box". That is, the fibers in the transmitter/detector device arrays receive transmitted optical energy, send the energy to the "breast box" imaging array via an optical coupling 222, 224, 226, 228 and the "breast box" imaging arrays fibers send the energy into the "breast box", and thus the patient's breast tissue. The energy exiting the patient's breast tissue is received by the fibers in the "breast box" imaging arrays and the energy is sent to the transmitter/detector device arrays. The energy exits the fibers in the transmitter/detector device arrays and is detected by an optical energy detector.

In a preferred embodiment, the transmitter/detector device 210 is connected to a data acquisition system 130. The data acquisition system 130 may be, for example, a computer. The data acquisition system 130 coordinates the transmission and detection of the optical energy and converts the detected energy into useful information, such as an image. The data acquisition system 130 may be connected to an output device, such as a monitor 140, VCR 150, or other memory device 160.

The invention preferably operates in the following manner. A patient's breast 115 is placed on the bottom array 202. The side and top arrays 204–208 are then positioned to gently touch the sides of the patient's breast 115. A block (not shown), such as a foam block may be inserted into the front of the "box". Note that little or no compression is necessary. This creates a "breast box" which encloses the breast that is ready for imaging.

Next, optical energy is sent from a transmitter into a transmitter/detector device array 212, 214, 216, 218 fiber and sent via fiber optic connection 222, 224, 226, 228 to a corresponding "breast box" array 202, 204, 206, 208 fiber. The transmitted energy is scanned throughout the patient's breast 115. Preferably, the optical energy is simultaneously transmitted by two transmitters in a synchronized manner so that the optical energy enters the patient's breast 115 at substantially orthogonal planes and "traces" a 3-dimensional grid throughout the patient's breast. The optical energy exiting the patient's breast along this grid is received by fibers in the "breast box" imaging arrays 202, 204, 206, 208. The received optical energy is then sent via fiber optic connection into a corresponding transmitter/detector array 120 fiber and detected by an optical energy detector.

Data regarding the optical energy input into and exiting out of the breast is provided to the data acquisition system 130. Using computer-tomography algorithms, the amount of energy entering and leaving each "block" of the 3-D grid may be determined. This information may be used for diagnosis. For example, an image of the breast tissue may be generated or photon absorption or scattering information may be used to determine the make-up of a suspicious mass. Also, the breast may be imaged using different wavelengths of optical energy in order to better determine the make-up of a suspicious mass.

II. The "Breast Box"

Figure 3A:
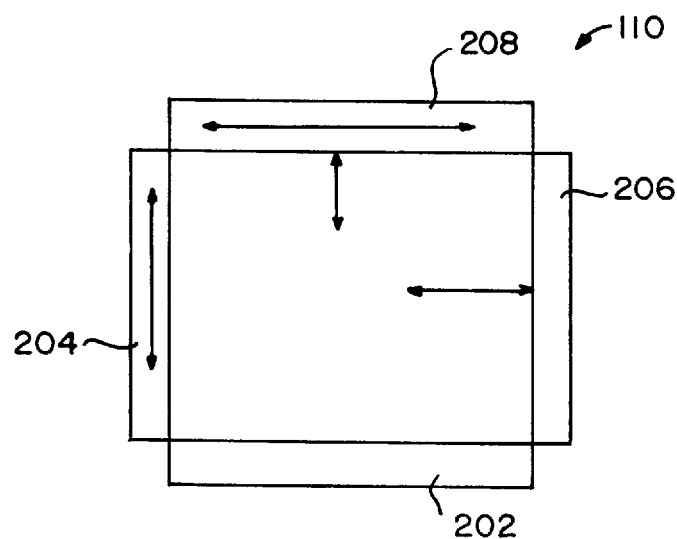
FIGS. 3A and 3B illustrate the adjustable positioning of "breast box" imaging arrays according to a preferred embodiment of the present invention.
Figure 3B:
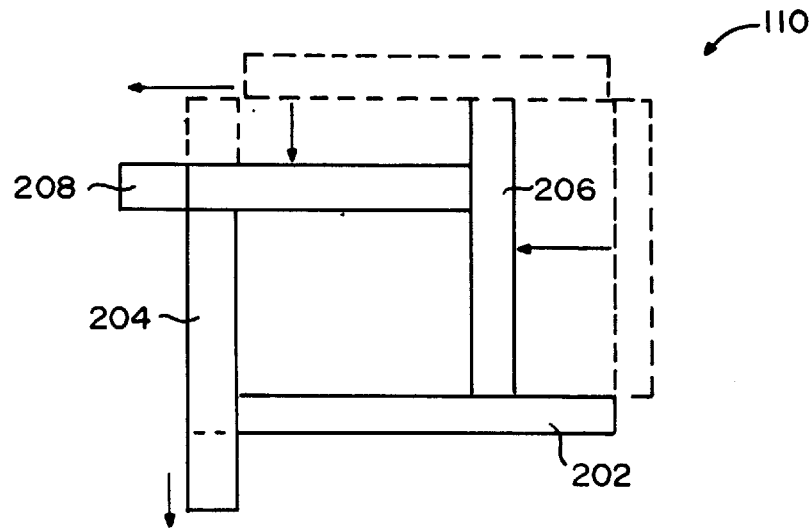

As seen in FIG. 2, the "breast box" preferably comprises four optical arrays 202–208, wherein the arrays are substantially orthogonal to the adjacent arrays. As seen in FIGS. 3A and 3B, three of these arrays 204–208 are preferably movable in order to accommodate different-sized breasts. FIG. 3A illustrates the arrays at their fully extended locations, providing a maximum volume. As indicated by the arrows, bottom array 202 is stationary, side array 204 moves in a vertical plane, side array 206 moves in a horizontal plane, and top array 208 moves both vertical and horizontal planes. FIG. 3B illustrates the arrays at an intermediate position. Note that in FIG. 3B, the arrays' positions in FIG. 3A are shown in phantom, and the direction and distance of movement is illustrated with arrows. A person skilled in the art readily appreciates that any number of mechanisms are suitable for providing the image array positioning.

Figure 4A:
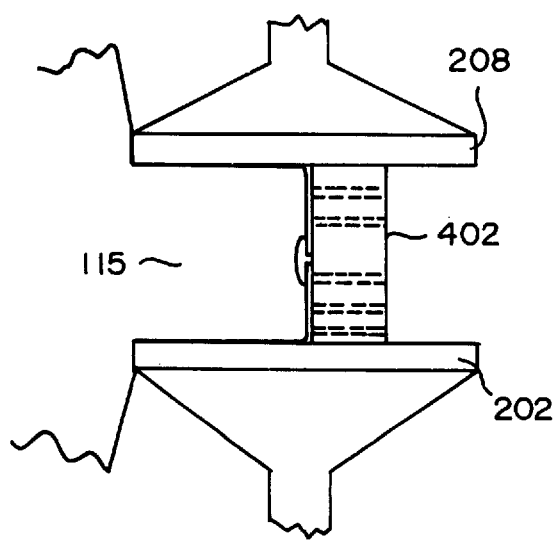
FIGS. 4A and 4B illustrate the positioning of the adjustable "breast box" imaging arrays around a patient's breast.
Figure 4B:
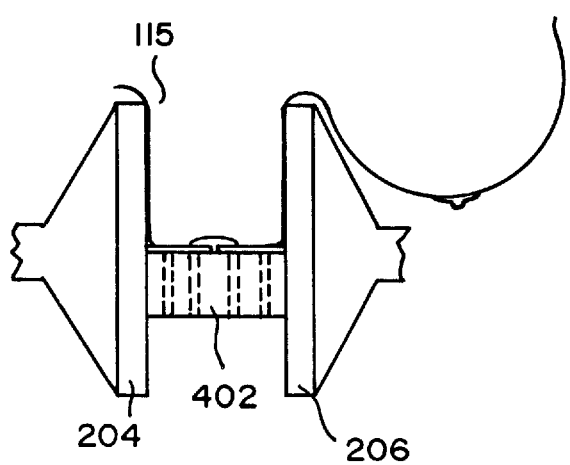

FIGS. 4A and 4B are side and top views, respectively, of a patient's breast 115 positioned in the "breast box". As seen in FIG. 4A, a patient's breast 115 is placed on a bottom array 202 and a top array 208 is positioned to contact the breast 115. A block 402 may be inserted to "close" the box and conform the end of the breast to the volume defined by the arrays. Blocks of various sizes and shapes may be provided to accommodate different sized breasts. As seen in FIG. 4B, the patient's breast 115 is positioned between two side arrays 204, 206. The block 402 is shown. The block 402 may be a foam block and/or a biopsy needle jig. The block may include apertures (shown in phantom). The inventive imaging device may be used for real-time imaging during a needle biopsy or other surgical procedure and the surgeon may use the biopsy needle jig to stabilize and/or properly locate the needle.

To align future breast images with a current breast image, a small permanent or temporary marker opaque to the imaging device (and preferably located away from a location of any suspicious mass so as not to obscure this portion of the image) may be placed on the patient's breast. This permits a reference point to correlate future images with previous images.

Preferably, the patient should be stabilized to keep from moving during the imaging process because any movement of the patient's breast during imaging may affect the clarity of the image. The patient may be stabilized by placing the patient in a chair with a head rest and perhaps a strap. Alternatively, the patient may by in a prone position—such as lying on a table with a hole in it—with her breast hanging down into the "breast box".

III. The Transmitter/Detector Device

Figure 5A:
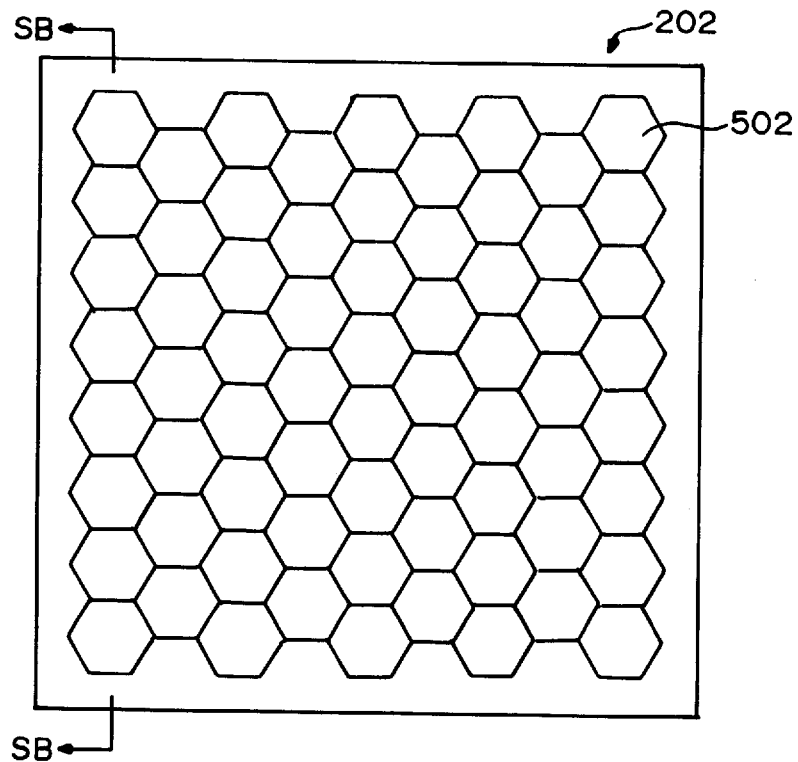
FIG. 5A is a front elevational view of a "breast box" imaging array according to a preferred embodiment of the present invention.
Figure 5B:
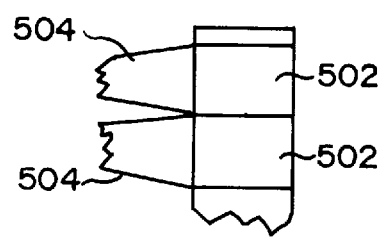
FIG. 5B is a partial cutaway view of the array of FIG. 5A taken along lines 5B—5B.
Figure 5B:
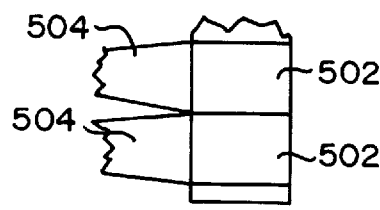

In a preferred embodiment of the present invention, the "breast box" is optically connected to a transmitter/detector device 120. Preferably, the four "breast box" imaging arrays 202, 204, 206, 208 include optical fibers (or fiber optic bundles) which are connected via fiber optic connections 222, 224, 226, 228 to a transmitter/detector device 120. FIGS. 5A and 5B illustrate a "breast box" imaging array according to this preferred embodiment, for example the bottom array 202.

FIG. 5A is a front elevational view of an illustrative "breast box" imaging array 202. The array 202 comprises a number of optical fibers (or fiber optic bundles) 502 which terminate on a surface of the array. To best use the imaging array surface, the optical fibers 502 may be hexagonal in cross-section. Optical energy may exit or enter the fibers 502 along this surface. These fibers 502 may be arranged in a number of horizontal rows and vertical columns, or in any desired arrangement. Note that a preferred embodiment of the invention, these fibers 502 may be very closely spaced to provide the necessary resolution for breast imaging.

FIG. 5B is a partial cutaway view of the array 202 taken along lines 5B—5B. A number of fibers 502 from a vertical column are seen. The fibers 502 are the terminal ends of optical fibers 504. These optical fibers may be combined into a single fiber optic connection 222 which is connected to a transmitter/detector device 120 array, such as array 212, as seen in FIG. 2 above and FIG. 6B below.

Figure 6A:
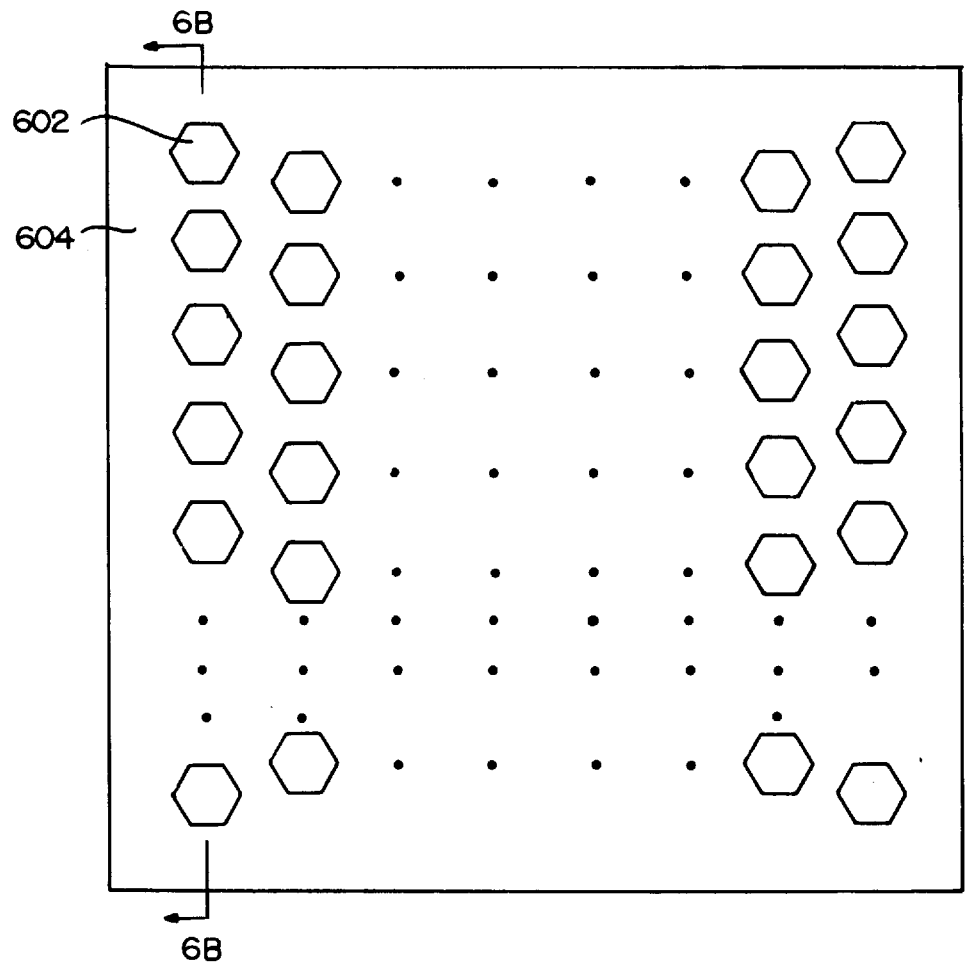
FIG. 6A is a front elevational view of a transmitter/detector device array according to a preferred embodiment of the present invention.

Each of the "breast box" imaging arrays is optically connected to a transmitter/detector device array. FIG. 6A is a front elevational view of an illustrative transmitter/detector device array 212. The array 212 comprises a number of optical fibers (or fiber optic bundles) 602 which terminate on a surface of the array. Optical energy may exit or enter the fibers 602 along this surface. As is described in more detail below, the transmitter/detector arrays 212, 214, 216, 218 are used to send optical energy to and receive optical energy from the "breast box" imaging arrays. The fibers 602 may be arranged in any desired manner. Preferably, the fibers 602 are arranged in a manner that corresponds to an associated fiber 502 in a "breast box" imaging array, such as array 202 as seen in FIG. 5A. Close spacing of the fibers 602 is not required because the transmitter/detector device arrays 212, 214, 216, 218 are not actually directly imaging the breast, but rather are only providing input to and output from the arrays 202, 204, 206, 208 in the "breast box" 110. Thus, inactive spaces 604 may be provided between the fibers 602.

Figure 6B:
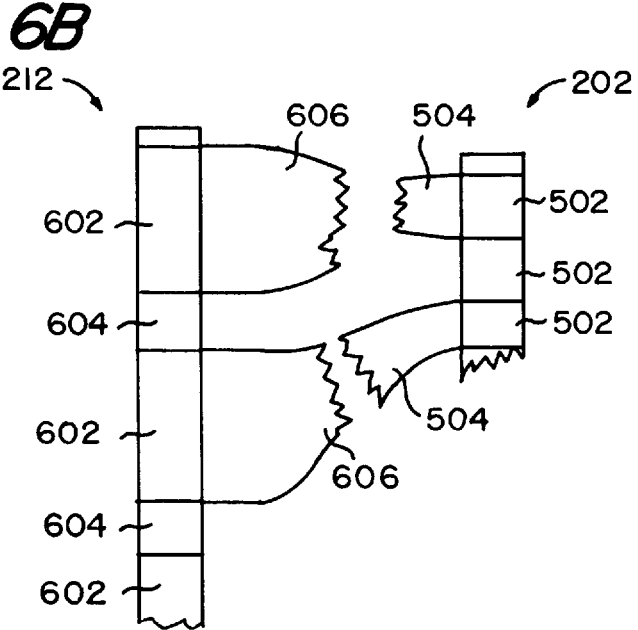
FIG. 6B is a partial cutaway view of the array of FIG. 6A taken along lines 6B—6B and illustrating a connection to the "breast box" imaging array shown in FIGS. 5A and 5B.

FIG. 6B is a partial cutaway view of the array 202 taken along lines 6B—6B and illustrating the connection between the "breast box" imaging array 202 and the transmitter/detector array 212. A number of fibers 602 from a vertical column are seen. The fibers 602 are the terminal ends of optical fibers 606. These optical fibers 606 are connected to the optical fibers 502 connected to the "breast box" imaging array. These optical fibers may be combined into a single fiber optic connection 222 connecting the transmitter/detector device array 212 with a corresponding "breast box" imaging array 202. Note that in a preferred embodiment, the optical fibers' diameter tapers from the transmitter/detector device array 212 to the "breast box" imaging array 202. In this manner, the diameter of the transmitter/ detector array fibers 602 may be greater than the "breast box" imaging array fibers 502.

Figure 7A:
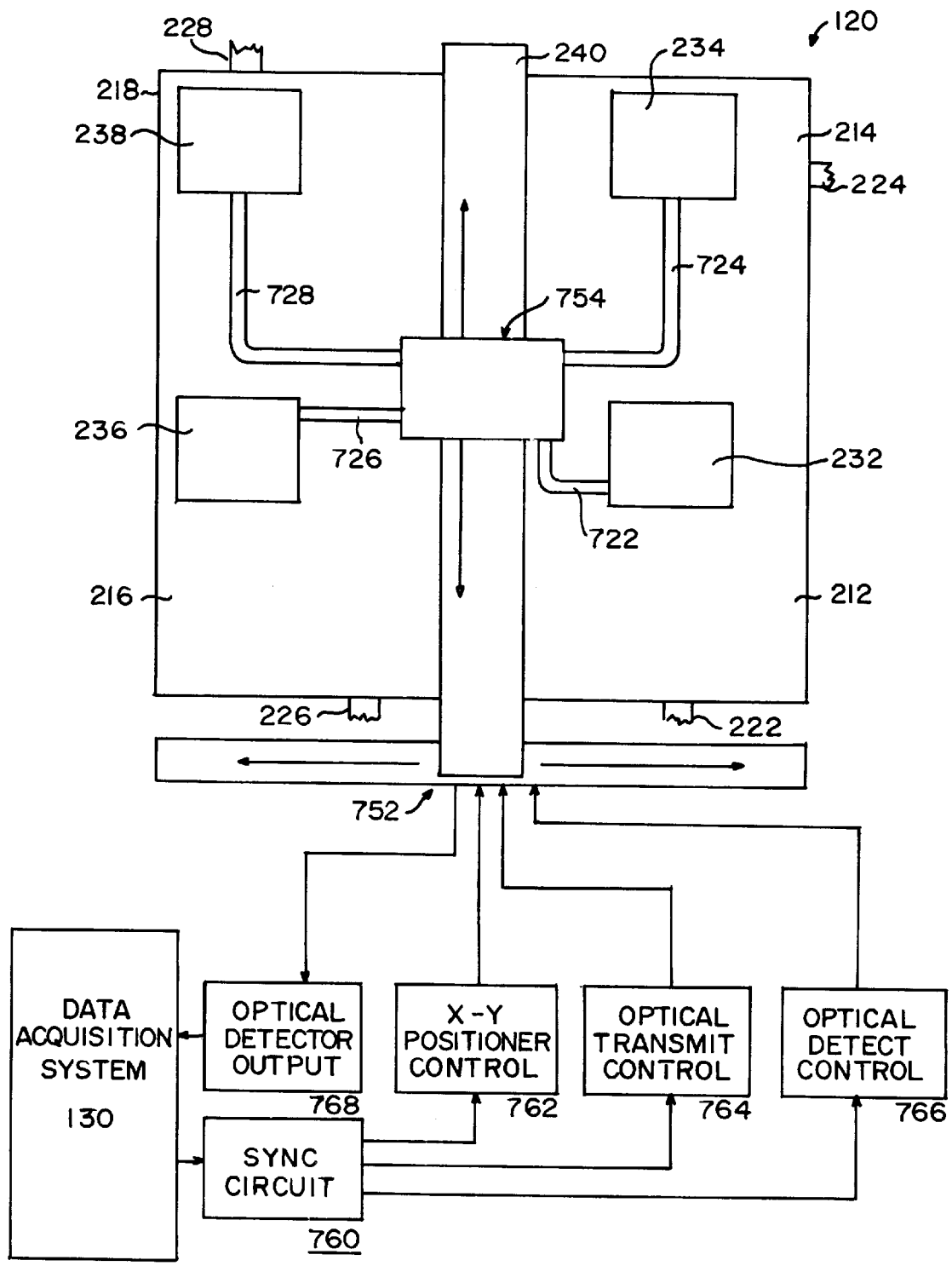
FIG. 7A is a front elevational view of a transmitter/detector device according to a preferred embodiment according to the present invention.
Figure 7B:
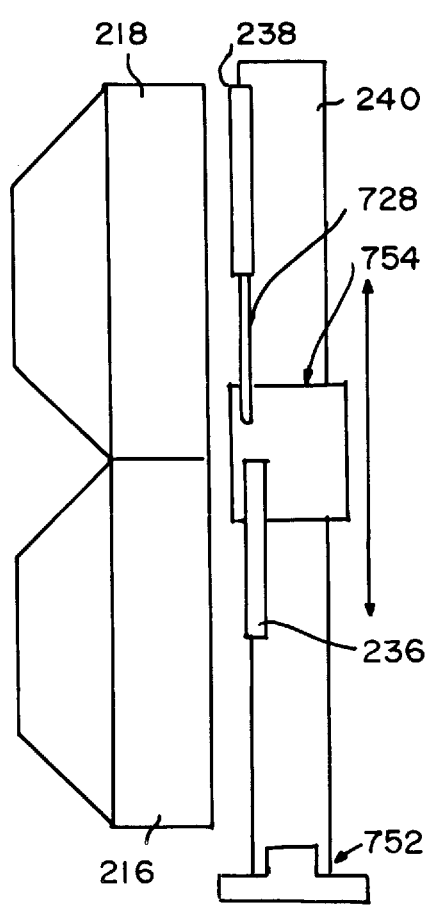
FIG. 7B is a side elevational view of the transmitter/detector device of FIG. 7A.

In addition to the four arrays 212, 214, 216, 218, the transmitter/detector device also includes one or more selectably positionable optical energy transmitters and optical energy detectors. The manner in which the transmitters and detectors are selectively positioned along the transmitter/detector arrays is described. FIGS. 7A and 7B illustrate a preferred embodiment of a transmitter/detector device 120 according to a preferred embodiment of the present invention. FIG. 7A is a front elevational view of a preferred transmitter/detector device 120. FIG. 7B is a side elevational view of the device 120 seen in FIG. 7A.

As seen in FIG. 7A, the device 120 includes the four arrays 212, 214, 216, 218 (each of which is connected to a "breast box" imaging array by a fiber optic connection 222, 224, 226, 228), x-y positioner 240, and four transmitter/detector units 232, 234, 236, 238. The transmitter/detector units are connected to the x-y positioner 240 via arms 722, 724, 726, 728. As best seen in FIG. 7B, the x-y positioner 240 and transmitter/detector units 232, 234, 236, 238 are located in close proximity to (or in contact with) the surfaces of the four arrays 212, 214, 216, 218 on which the fibers 602 are located. In a preferred embodiment, the transmitter/detector device 120 is contained in a sealed, opaque box to prevent ambient light from affecting the imaging.

As illustrated by the arrows in FIGS. 7A and 7B, the x-y positioner moves in the x and y directions (i.e., the horizontal and vertical directions, respectively) in order to position the transmitter/detector units 232, 234, 236, 238 at different locations on the arrays. The x-y positioner 240 may be two mechanical motion devices 752, 754. This first device provides motion in a first direction, such as the x direction. The entire first motion device 752 may be connected to the second mechanical motion device 754, which moves along the first motion device 752 in a second direction substantially orthogonal to the first direction (i.e., the y direction). These mechanical motion devices 752 may be, for example, the advanced linear motion products provided by Thompson Industries, Inc.

Note that in FIGS. 7A and 7B, the x-y positioner is located in the upper-most and leftmost position. Thus, the x-y positioner will move to the right and down in order to be located at different locations on the array. The transmitter/detector units are configured to (1) transmit optical energy into the fibers on the surface of the transmitter/detector arrays 212, 214, 216, 218 which are sent to the "breast box" imaging arrays 202, 204, 206, 208 via fiber optic connections 222, 224, 226, 228; and (2) detect optical energy which was received by the fibers 502 in the "breast box" imaging array and which are sent to the transmitter/detector device arrays via the fiber optic connections.

As seen in FIG. 7A, the movement of the transmitter/detector device 120, and the operation of the transmitters and detectors are responsive to a sync circuit 760. The sync circuit 760 may be part of the data acquisition system 130. The sync circuit 760 controls the movement of the motion devices 752, 754, via an x-y positioner control circuit 762. The sync circuit also controls the firing of the optical energy transmitters via an optical transmit control circuit 764. Preferably, the sync circuit may also control the operation of the optical energy detectors via an optical detect control circuit 766. Thus, the time and location of optical energy transmissions, and the operation of detectors may be precisely controlled. Note that although breast imaging has very stringent imaging requirements, the distance traveled between transmitter firings does not need to be very small because the transmitter/detector arrays may have larger diameter fibers and be spaced further apart than the fibers in the "breast box" imaging arrays. Thus, accuracy of the x-y positioner to distances as small as several hundred microns is unnecessary because the transmitter/detector arrays are "scaled up" versions of the "breast box" imaging arrays, as described above.

The output of the detectors may be sent to an optical detector output circuit 768, which may provide the detector output to the data acquisition system 130. Alternatively, the optical detector output circuit 768 may be part of the data acquisition system 130.

Figure 8A:
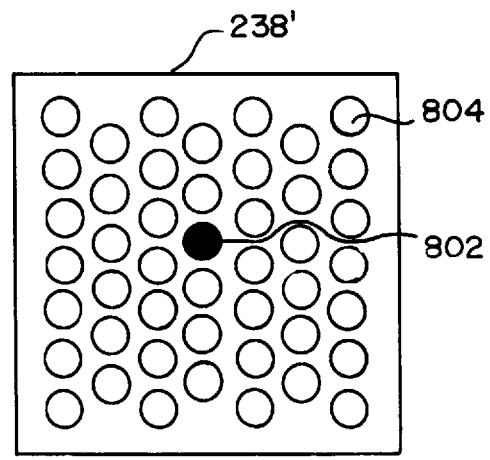
FIGS. 8A and 8B illustrate two preferred embodiments of transmitter/detector units according to the present invention.
Figure 8B:
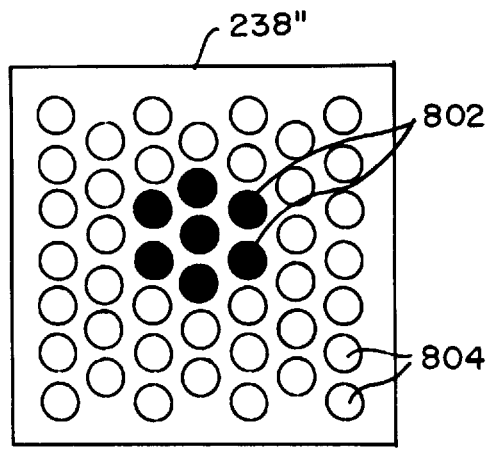

FIGS. 8A and 8B illustrate two alternative embodiments of a transmitter/detector unit 238 according to a preferred embodiment of the present invention. As seen in FIG. 8A, a first embodiment of a transmitter/detector unit 238' includes a single optical transmitter 802 (illustrated as a black dot). The optical transmitter 802 may be any suitable optical energy source, such as a laser or light emitting diode. The transmitter/detector unit 238' includes a number of detectors 804 (illustrated as white dots). The detectors may be any suitable optical energy detector, such as photodiodes or charged coupled devices. As seen in FIG. 8B, a transmitter/detector unit 238" may include a number of transmitters 802. These transmitters may transmit optical energy of different wavelengths. Because different wavelengths of energy have different absorption and scatter characteristics, imaging the patient's breast with different energy wavelengths may provide information determining the make-up of a suspicious mass. Other alternative configurations for the transmitter/detector units are readily appreciated by the skilled practitioner.

Note that three dimensional scanning of the breast may be performed by moving the optical energy transmitters and detectors in only two directions (i.e., the x and y directions).

IV. The Scanning and Detecting Processes

As described above, the movement of the x-y positioner, the firing of the optical transmitters, and the operation of the detectors are synchronized so that the breast imaging device data acquisition system 130 may determine from which transmitter optical energy is being transmitted and at which detector or detectors optical energy is being received.

Figure 9A:
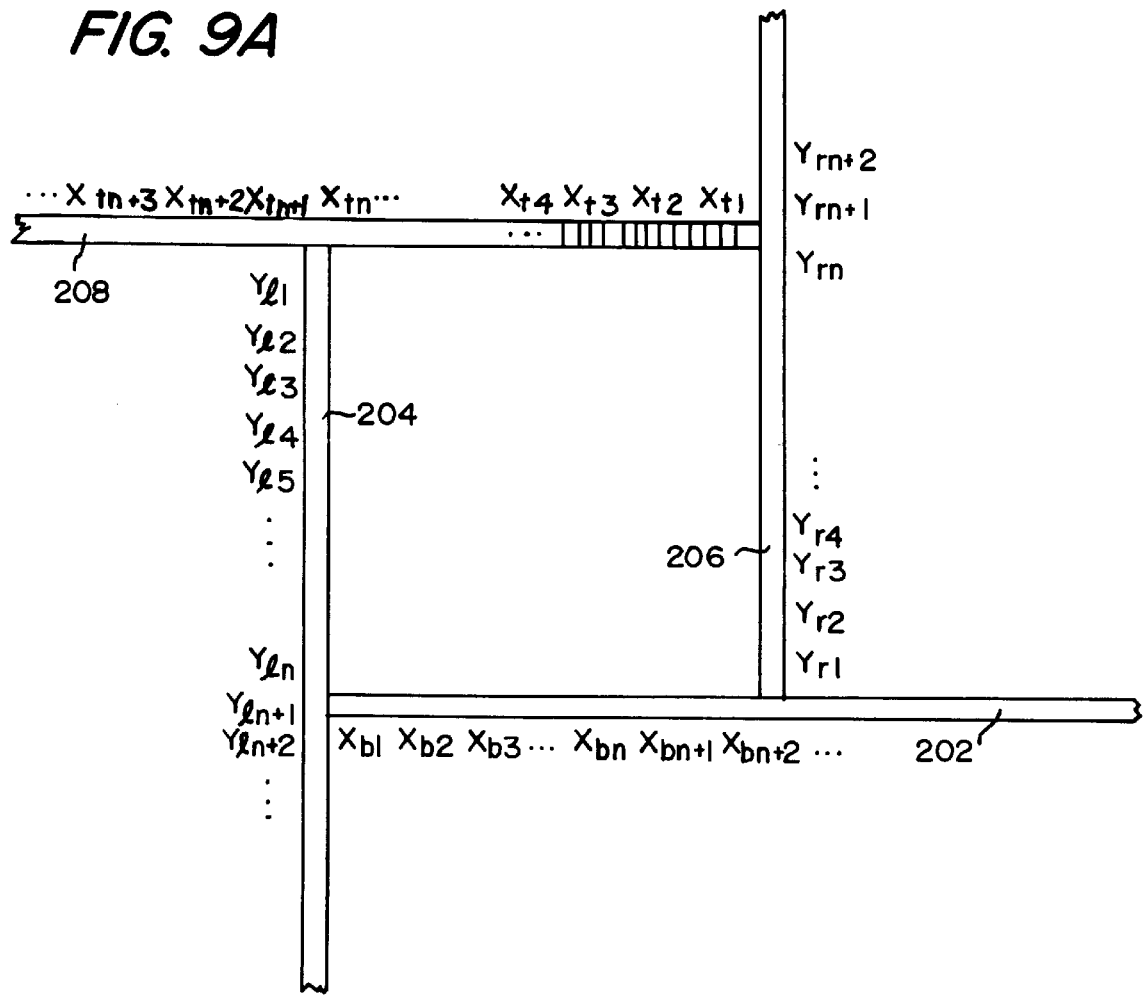
FIGS. 9A and 9B illustrate the scanning process performed by the arrays.
Figure 9B:
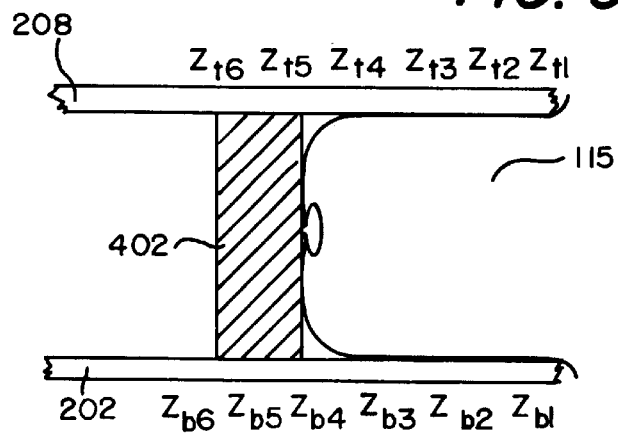

FIGS. 9A and 9B illustrate the scanning process performed by the present invention. FIG. 9A is a front view of arrays 202–208. Each figure shows a row of fibers 502 which may send or receive optical energy. In a first direction, illustratively the x direction, top array 208 has a row of optical fibers $x_{t1}, x_{t2}, x_{t3}, \ldots x_{tn} \ldots$ In the same direction, bottom array 202 has a corresponding set of fibers $x_{b1}, x_{b2}, x_{b3}, \ldots x_{bn} \ldots$ In a second direction, illustratively the y direction, left side array 204 has a row of fibers $y_{l1}, y_{l2}, y_{l3}, \ldots y_{ln} \ldots$ In the same direction, right side array 206 has a row of optical detectors $y_{r1}, y_{r2}, y_{r3}, \ldots y_{rn} \ldots$ FIG. 9B is a side view of top and bottom arrays 202, 208, each showing a row of fibers. In a third direction, illustratively the z direction, the top array 208 has a row of fibers $z_{t1}, z_{t2}, z_{t3}, \ldots z_{tn} \ldots$ (Note that these fibers may also be in an x-direction row seen in FIG. 9A.) In the same direction, the bottom array 202 has a corresponding row of fibers $z_{b1}, z_{b2}, z_{b3}, \ldots z_{bn} \ldots$ (These fibers may also be in an x-direction row seen in FIG. 9A.)

During the transmission process, the transmitter/detector sequence may occur in the following manner. If optical energy is sent by a fiber $z_{t1}, x_{t1}$, a portion of the transmitted optical energy will be received at the opposite fibers $z_{b1}, x_{bn}$. (Note that in this example, $z_{t1}$ and $x_{t1}$ are the same fiber on top array 208 and $z_{b1}$ and $x_{b1}$ are the same fiber on bottom array 202). A portion of the optical energy may be reflected back due to a collision with certain types of tissue located in the energy's path and be received by the top array 202, for example, fiber $x_{t2}, z_{t2}$. Other energy may be absorbed by certain types of tissue in the energy's path, or received by other fibers.

Alternatively, two substantially orthogonal transmitters 802 may be fired simultaneously. Optical energy may be transmitted simultaneously in the x and y directions so that the two transmitted energy "beams" cross in a particular location in the patient's breast. The transmitted energy may be scanned in a synchronized manner so that the optical energy "traces" a 3-dimensional grid throughout the patient's breast 115.

The process may be completed, for example, when $x_{b1}$ and $y_{r1}$ detect a certain level of optical energy, indicating that optical energy is being sent by optical fibers directly across from these fibers. As seen in FIG. 9A, these should be the last two fibers to receive transmitted optical energy. A person skilled in the art readily appreciates that the process may be determined to be completed in a number of suitable ways.

The inputs and outputs of these fibers are provided to the data acquisition system 130 and processed in a manner described below to determine the absorption and/or scattering of the transmitted optical energy.

V. The Data Acquisition System

Figure 10:
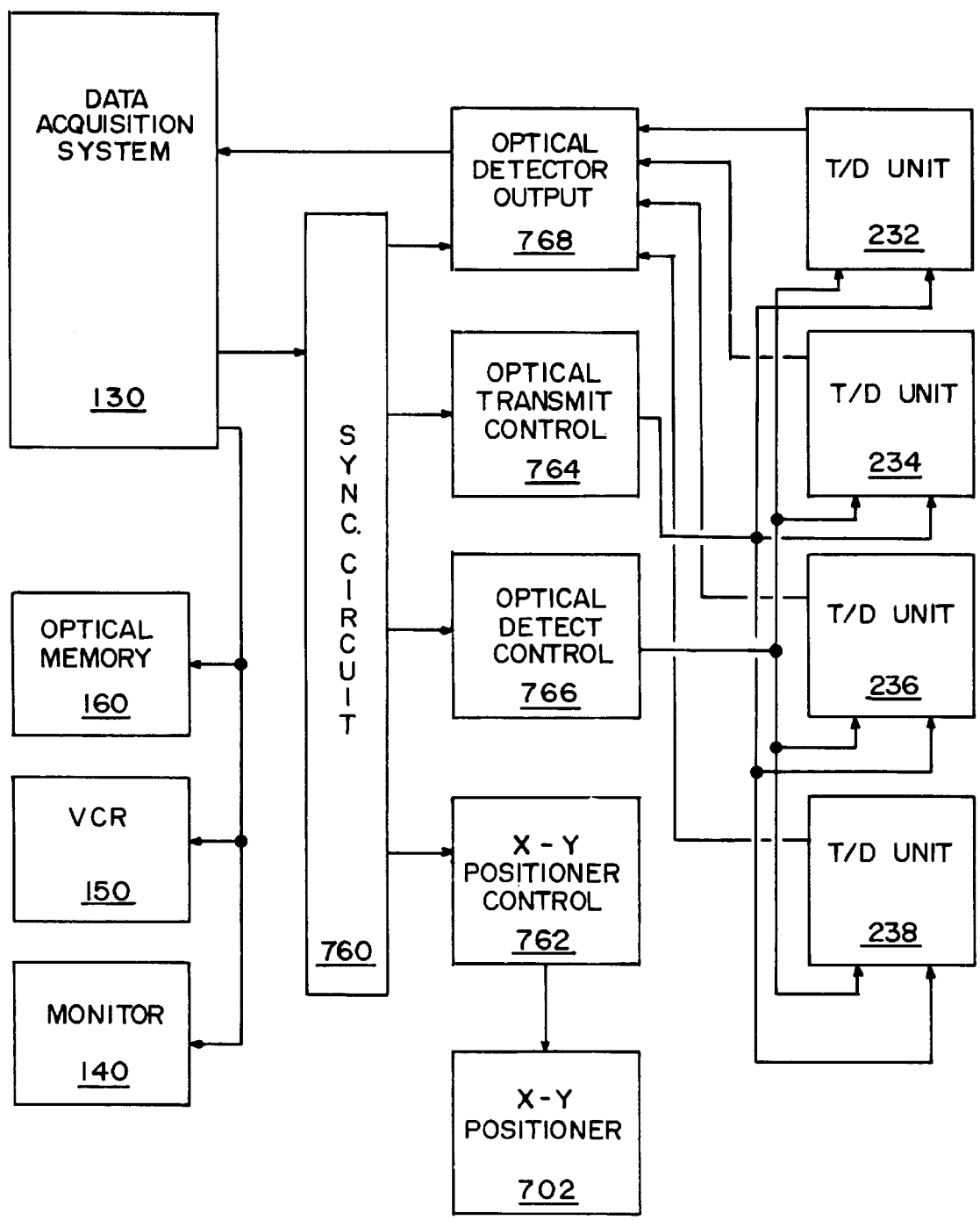
FIG. 10 is a block diagram of a preferred embodiment of a data acquisition system according to the present invention.

The data acquisition system 130 receives and processes the information generated by scanning the patient's breast with optical energy. The data acquisition system may be any system suitable for converting the detector output into useful information, such as an image. FIG. 10 is a block diagram of a preferred embodiment of a data acquisition system 130 according to the present invention. The data acquisition system (DAS) 130 may control a sync circuit 760 which in turn may control an optical transmit control circuit 764 and optical detect control circuit 766. These circuits may control the operation of the transmission/detection units 232, 234, 236, 238. The sync control circuit 760 may also control an x-y positioner control circuit 762 which in turn may control the movement of the positioner 240. The data obtained by the detectors may be sent to the DAS via an optical detector output circuit 768.

The received data may be processed in a well known manner to provide useful information. For example, computations for converting raw information about transmitted and received energy into useful information are commonly used in computed tomography. See, for example, *Christensen's Physics of Diagnostic Radiology* (4th Ed.), pp. 301–02 (Lea & Febiger, 1990). Data regarding the optical energy input into and exiting out of the breast is provided to the data acquisition system. Using well-known computer-tomography algorithms (such as described above), the amount of energy entering and leaving a portion (or "block") of the 3-D grid may be determined. This information indicates the amount of energy that was absorbed, scattered, or passed through the "block" and may be used to generate an image of that "block" and/or may be used for diagnosis. The processed data may be output as an image to a monitor 140, a VCR 150, or a memory device 160.

This processed data may be viewed by a skilled professional, such as a radiologist or other physician, for interpretation. Because the data is in digital form, it may be saved, transmitted, processed or otherwise handled in the same manner as any other digital data. It may, for example, be transmitted over telephone or optical fiber lines to a remote location so that another expert, perhaps in another city or country, may also examine the image. Also, because the information is digital, the image may be enlarged without significant distortion up to the limits of the device's resolution.

VI. Conclusion

Described is an optical breast imaging device. The device uses no ionizing radiation and does not require the patient's breast to be compressed. The entire scanning process may be done comfortably. The present invention may be used as a primary or adjunctive diagnostic tool. It is believed that the inventive system has a resolution as fine as 3 microns, depending on the optical wavelength used.

The above described embodiments of the invention are intended to be illustrative only. Numerous alternative embodiments may be devised by those skilled in the art without departing from the spirit and scope of the following claims. For example, the invention may be used for other types of diagnostic imaging. Because breast imaging has particularly stringent requirements, a person skilled in the art readily understands that the invention may be used for other imaging systems, as well.

I claim:

1. A breast imaging device, comprising:
   (a) four imaging arrays, each imaging array being orthogonal to two adjacent imaging arrays and each imaging array having an inner surface including a number of optical fibers configured to send and to receive optical energy and wherein the imaging arrays are arranged to define a volume in which a breast may be enclosed; and
   (b) a data acquisition system configured to generate an image in response to information received from the four imaging arrays.

2. The device of claim 1, wherein the imaging arrays are configured to be selectively adjusted to accommodate different sized breasts.

3. The device of claim 1, wherein a first of the four imaging arrays is stationary, a second of the four imaging arrays moves in a first plane, a third of the four imaging arrays moves in a second plane opposite the first plane, and a fourth of the four imaging arrays moves in the first and second planes.

4. The device of claim 1, further including a block configured to enclose the volume in which the breast may be enclosed.

5. The device of claim 4, wherein the block is a biopsy jig.

6. The device of claim 4, wherein the block includes at least one aperture configured to receive a biopsy needle.

7. The breast imaging device of claim 1, further comprising a transmitter/detector device connected between the imaging arrays and the data acquisition device, the transmitter/detector device configured to transmit optical energy to and receive optical energy from the imaging arrays and to transmit information to and receive information from the data acquisition system.

8. The breast imaging device of claim 1, wherein the data acquisition system further comprises an output device.

9. The breast imaging device of claim 8, wherein the output device is a monitor.

10. A breast imaging device, comprising:
    (a) a plurality of imaging arrays, each imaging array having an inner surface including a number of optical fibers configured to send and to receive optical energy and wherein the imaging arrays are arranged to define a volume in which a breast may be enclosed;
    (b) a plurality of transmitter/detector arrays each having a surface including a number of optical fibers and wherein each imaging array optical fiber is optically connected to a transmitter/detector array optical fiber; and
    (c) a data acquisition system configured to generate an image in response to information received from the transmitter/detector device.

11. The breast imaging device of claim 10, wherein the data acquisition system further comprises an output device.

12. The breast imaging device of claim 11, wherein the output device is a monitor.

13. The device of claim 10, wherein a diameter of the transmitter/detector array optical fibers is greater than a diameter of the imaging array optical fibers.

14. The device of claim 10, wherein the transmitter/detector array optical fibers are configured to receive optical energy and to send the optical energy to the imaging array optical fibers.

15. The device of claim 10, further including an optical energy transmitter configured to transmit optical energy into a transmitter/detector array optical fiber.

16. The device of claim 15, wherein the transmitter is configured to transmit optical energy having a plurality of wavelengths.

17. The device of claim 10, wherein the imaging array optical fibers are configured to receive optical energy and to send the optical energy to the transmitter/detector array optical fibers.

18. The device of claim 17, further including an optical energy detector configured to detect optical energy sent from an imaging array optical fiber to a transmitter/detector array optical fiber.

19. The device of claim 10, further comprising:
    a. at least one transmitter/detector unit, comprising:
       (1) an optical energy transmitter configured to transmit optical energy into a transmitter/detector array optical fiber;
       (2) an optical energy detector configured to detect optical energy sent to a transmitter/detector array optical fiber; and
    b. a positioner configured to selectively position the optical energy transmitter and optical energy detector at desired locations along the surfaces of the plurality of transmitter/detector arrays.

20. The device of claim 19, wherein the positioner further comprises a first motion device configured to move in a first plane and a second motion device connected to the first motion device configured to move in a second plane.

21. The device of claim 19, wherein the transmitter/detector array surfaces are configured to allow the positioner to move only in two planes.

22. The device of claim 19, further comprising a sync circuit connected to the positioner and the optical energy transmitter, the circuit configured to synchronize movement of the positioner and operation of the transmitter.

23. The device of claim 19, wherein the sync circuit is connected to the optical energy detector and is configured to synchronize the operation of the optical energy detector with the operation of the transmitter.

24. A device for transmitting optical energy into and detecting optical energy from a patient's tissue, the device adapted for connection to a data acquisition device, comprising:
    a. a plurality of imaging arrays configured to define a volume in which the patient's tissue may be enclosed, each array including a number of optical fibers configured to send and receive optical energy;
    b. a plurality of transmitter/detector arrays having a surface including a number of optical fibers and wherein each imaging array optical fiber is optically connected to a transmitter/detector array optical fiber;

c. at least one transmitter/detector unit, comprising:
   (1) an optical energy transmitter configured to transmit optical energy into a transmitter/detector array optical fiber;
   (2) an optical energy detector configured to detect optical energy sent to a transmitter/detector array optical fiber from an imaging array fiber; and d. a positioner configured to selectively position the optical energy transmitter and optical energy detector at desired locations alone the surfaces of the plurality of transmitter/detector arrays.

25. The device of claim 24, wherein the positioner further comprises a first motion device configured to move in a first plane and a second motion device connected to the first motion device configured to move in a second plane.

26. The device of claim 24, wherein the transmitter/detector array surfaces are configured to permit the positioner to move only in two planes.

27. The device of claim 24, further comprising a sync circuit connected to the positioner and the optical energy transmitter, the circuit configured to synchronize movement of the positioner and operation of the transmitter.

28. The device of claim 27, wherein the sync circuit is connected to the optical energy detector and is configured to synchronize the operation of the optical energy detector with the operation of the transmitter.

29. The device of claim 24, further comprising two transmitters configured to transmit simultaneously energy beams, the two transmitters arranged in a manner so that the energy beams cross in a predetermined location in the patient's tissue.

30. The device of claim 29, wherein the transmitters are configured to transmit the energy beams in a same plane and the energy beams enter the patient's tissue at substantially orthogonal planes.

31. The device of claim 24, wherein the imaging arrays are configured to be selectively adjusted to accommodate different volumes.

32. The device of claim 24, wherein the imaging device includes four imaging arrays, each imaging array being orthogonal to two adjacent arrays.

33. The device of claim 32, wherein a first of the four imaging arrays is stationary, a second of the four imaging arrays moves in a first plane, a third of the four imaging arrays moves in a second plane opposite the first plane, and a fourth of the four imaging arrays moves in the first and second planes.

34. The device of claim 24, further comprising a data acquisition system connected to receive data from the optical energy detectors and to process the received data.

35. The device of claim 34, wherein the data acquisition system is configured to convert the received data into an image.

* * * * *